United States Patent
Kurotobi et al.

(10) Patent No.: US 11,567,046 B2
(45) Date of Patent: Jan. 31, 2023

(54) DATA-PROCESSING DEVICE FOR CHROMATOGRAPH

(71) Applicant: SHIMADZU CORPORATION, Kyoto (JP)

(72) Inventors: Futoshi Kurotobi, Kyoto (JP); Toshikazu Minohata, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 815 days.

(21) Appl. No.: 16/473,739

(22) PCT Filed: Mar. 17, 2017

(86) PCT No.: PCT/JP2017/011068
§ 371 (c)(1),
(2) Date: Jun. 26, 2019

(87) PCT Pub. No.: WO2018/167986
PCT Pub. Date: Sep. 20, 2018

(65) Prior Publication Data
US 2019/0353627 A1    Nov. 21, 2019

(51) Int. Cl.
*G01N 30/86* (2006.01)
*G01N 30/46* (2006.01)
(Continued)

(52) U.S. Cl.
CPC ....... *G01N 30/8631* (2013.01); *G01N 30/468* (2013.01); *G01N 30/6034* (2013.01);
(Continued)

(58) Field of Classification Search
CPC ............. G01N 30/8631; G01N 30/468; G01N 30/6034; G01N 30/88; G01N 33/68;
(Continued)

(56) References Cited

U.S. PATENT DOCUMENTS 6,029,495 A    2/2000  Munetaka
7,178,386 B1 * 2/2007  Gamble ............. G01N 30/8665
                                                      73/61.52
(Continued)

FOREIGN PATENT DOCUMENTS

JP    10-318803 A    12/1998
JP    11-023556 A    1/1999
(Continued)

OTHER PUBLICATIONS

Communication dated Feb. 3, 2020, from the European Patent Office in European Application No. 17900895.8.
(Continued)

*Primary Examiner* — Jennifer Wecker
*Assistant Examiner* — Michael Paul Shimek
(74) *Attorney, Agent, or Firm* — Sughrue Mion, PLLC (57) ABSTRACT

The present invention is a data-processing device used for a chromatograph which continuously performs a series of analyses for components in each sample while sequentially introducing a plurality of samples into a column. The device includes: an input section configured to allow for input of information into a schedule table for a plurality of analyses, the schedule table describing an analysis condition including a combination of the values of a plurality of control parameters, the order of execution of the plurality of analyses, and information for identifying a sample to be subjected to each analysis; a chromatogram creating means configured to receive data sequentially collected during two or more analyses and create a joint chromatogram from the data if the two or more analyses have been continuously performed for the same sample according to the schedule table; and a display means configured to display the joint chromatogram.

6 Claims, 5 Drawing Sheets

(51) Int. Cl.
*G01N 30/60* (2006.01)
*G01N 30/88* (2006.01)
*G01N 33/68* (2006.01)

(52) U.S. Cl.
CPC ............. *G01N 30/88* (2013.01); *G01N 33/68* (2013.01); *G01N 2030/8818* (2013.01)

(58) Field of Classification Search
CPC ......... G01N 2030/8818; G01N 30/466; G01N 30/8651; G01N 30/8655; G01N 35/0092; G01N 30/24
See application file for complete search history.

(56) References Cited

U.S. PATENT DOCUMENTS

| | | |
|---|---|---|
| 2014/0157878 A1 | 6/2014 | Ohashi et al. |
| 2015/0066388 A1* | 3/2015 | Katsuyama ........ G01N 30/8658 702/31 |
| 2015/0253294 A1 | 9/2015 | Ohashi |
| 2018/0045690 A1 | 2/2018 | Hamase et al. |

FOREIGN PATENT DOCUMENTS

| | | | |
|---|---|---|---|
| JP | 2005-3558 A | | 1/2005 |
| JP | 2005003558 A | * | 1/2005 |
| JP | 2005-127814 A | | 5/2005 |
| JP | 2005127814 A | * | 5/2005 |
| JP | 2012-193999 A | | 10/2012 |
| JP | 2015-166725 A | | 9/2015 |
| WO | 2016/181956 A1 | | 11/2016 |

OTHER PUBLICATIONS

Written Opinion for PCT/JP2017/011068, dated Jun. 13, 2017.
International Search Report for PCT/JP2017/011068, dated Jun. 13, 2017.
Office Action dated Apr. 28, 2020 in Japanese Application No. 2019-505678.

* cited by examiner

| HPLC | : | Prominence LC System |
|---|---|---|
| Column | : | CROWNPAK CR-I(+)/(-) (3 mmI.D. x 150 mmL., 5μm |
| Column Temperature | : | 25 C |
| Mobile Phase | : | Acetonitrile/Etahnol/Water/TFA=80/15/5/0.5 |
| Flow Velocity | : | 0.6 mL/min |
| Amount of Injection | : | 1 μL |
| Analysis Period | : | 10.0 min |

Fig. 6B

| LC/MS/MS | : | LCMS-8050 |
|---|---|---|
| Nebulizer Gas Flow Rate | : | 3.0 L/min |
| Dry Gas Flow Rate | : | 15.0 L/min |
| Heating Gas Flow Rate | : | 5.0 L/min |
| Interface Temperature | : | 250 C |
| DL Temperature | : | 250 C |
| Heat Block Temperature | : | 300 C |

DATA-PROCESSING DEVICE FOR CHROMATOGRAPH

CROSS REFERENCE TO RELATED APPLICATIONS

This Application is a National Stage of International Application No. PCT/JP2017/011068 filed Mar. 17, 2017.

TECHNICAL FIELD

The present invention relates to a data-processing device for a chromatograph, such as a liquid chromatograph (hereinafter abbreviated as the "LC") or gas chromatograph (hereinafter abbreviated as the "GC").

BACKGROUND ART

In a chromatographic analysis, a mobile phase (which may also be called an "eluate") and a sample injected into the mobile phase are passed through a column. The components in the sample are thereby separated from each other due to their difference in the interaction with the stationary phase (which may also be called a "packing material") and the mobile phase in the column, and are eventually detected with a detector. Based on the data collected with the detector, a chromatogram is created, with the horizontal axis indicating the retention time of each component isolated by the column and the vertical axis indicating the relative intensity (concentration) of each component detected with the detector. A peak which corresponds to a component appears on the chromatogram for each component in the sample.

Such a chromatographic analysis is performed using the most suitable analyzing system and according to a previously determined analysis method which is the most suitable for the components contained in the sample. For example, the analysis method is determined by the kind of mobile phase, flow velocity of the mobile phase, temperature of the column oven and other relevant factors, while the analyzing system is determined by the type of column, for example. If the most suitable analysis method and analyzing system vary from one component to another contained in the sample, analyses using different analysis methods and different analyzing systems are performed for the same sample. An example of such an analysis is an analysis of monosaccharides, polyols and sterols in a biological sample which is performed using a high-performance liquid chromatograph mass spectrometer for the purpose of screening specific kinds of diseases caused by inborn errors of metabolism. Those monosaccharides, polyols and sterols need to be individually analyzed by different analysis methods and different analyzing systems. In other words, three analysis methods and three analyzing systems are used.

Another example is a quantitative analysis of the D-forms and L-forms of amino acids, in which columns that are suitable for optical isomer analysis are used, such as the CROWNPAK CR-I columns of Daicel Corporation. More specifically, two columns having different separation characteristics, CROWNPAK CR-I(+) and CROWNPAK CR-I (−), are used for the analysis. That is to say, two analyzing systems are used for the analysis.

Still another example is an analysis called the "method scouting", which is performed to search for optimum analysis conditions for a sample in an analytical technique using a high-performance liquid chromatograph. In the method scouting, an analysis for the same sample is continuously performed for a considerable period of time while variously changing both the analyzing system (column) and the analysis method (kind of mobile phase, flow velocity of the mobile phase, temperature of the column oven, and other factors).

A system named the Twin Line GC-MS System (manufactured by Shimadzu Corporation) has been commercially offered as a gas chromatograph mass spectrometer in which the exit ends of a plurality of columns having different separation characteristics are attached to the mass spectrometer to allow for the switching of the columns during an analysis while maintaining the degree of vacuum in the mass spectrometer. With this system, an analysis using a plurality of columns (analyzing systems) for the same sample can be continuously performed.

In any of the previously mentioned analyses, an automatic sample introduction device, such as an auto-sampler, is used to continuously perform the analysis by sequentially collecting a predetermined amount of sample from each of the prepared sample containers and introducing the collected sample into the mobile phase. For such an analysis, a schedule table which describes the identification number of the sample, analysis method, analyzing system, order of execution of the analysis and other related information is normally prepared. The analysis is performed multiple times while the introduction of the sample as well as the switching of the analysis method and the analyzing system are automatically performed according to the schedule table (Patent Literature 1). The analysis result obtained each time is collected as chromatogram data and contained in one data file created for each execution of the analysis of each sample. The file is stored in a storage device.

The beginning point of the chromatogram data is normally set at the point in time of the injection of the sample (or a point in time which is later than the point in time of injection by a specific length of time). Conventional LC data-processing devices continuously collect chromatogram data until the end of a predetermined data-collection period from the point in time of the beginning point, and compiles the data into one set to be contained in one data file. Accordingly, in such a conventional data-processing device, if the sample is injected N times, a total of N data files will be created even in the case where an analysis with different analyzing systems is continuously performed for the same sample, as in the Twin Line GC-MS System mentioned earlier.

CITATION LIST

Patent Literature

Patent Literature 1: JP 10-318803 A

SUMMARY OF INVENTION

Technical Problem

In the previously described data-processing device, since one data file is created for each injection of the sample (i.e. each injection of the sample is considered as the beginning of a new analysis), the same number of combinations of the analysis method and analyzing system as the number of data files are required. Each set of chromatogram data obtained for the analysis which are conducted according to a combination of the analysis method and analyzing system specified in the schedule table is saved as one separate data file. Therefore, although those data are obtained by analyses performed on the same sample, the data analysis must be performed on each separate data file. Accordingly, a number of data-analysis methods corresponding to the data files are required.

In the case where a plurality of analyses using the same analysis method are performed for the same sample, those analyses can be continuously performed even if different analyzing systems are used. In that case, the sample is injected every time the analyzing system is changed. Therefore, if the conventional data-processing device is used, it is not possible to guarantee that the chromatogram data obtained by the analyses using different analyzing systems have been obtained as the result of a series of analyses continuously performed on the same sample.

There are also other problematic situations associated with a temporal discontinuity between chromatograms. For example, a malfunction of the device may occur within the period between one analysis and the subsequent analysis in a series of analyses, with the result that an abnormality occurs in the chromatograms. Another example is the case where a third party with malicious intent has falsified a chromatogram corresponding to one analysis included in such in a series of analyses. In those cases, it is difficult to detect the abnormality in or falsification of the chromatogram since there is no temporal continuity between the successive chromatograms in the first place.

Thus, in a chromatographic analysis in which an analysis of various components in the same sample is continuously and repeatedly performed while fractions of the same sample are sequentially introduced into a column, the problem to be solved by the present invention is to provide a technique by which the data obtained with different analyzing systems for the same sample can be handled as a single set of data so that the temporal continuity of the chromatograms obtained through a series of analyses and the sameness of the sample are guaranteed, and an abnormality in or falsification of a chromatogram can be easily detected.

Solution to Problem

The present invention developed for solving the previously described problem is a data-processing device to be used for a chromatograph including a column, a sample-introducing section configured to introduce a sample into the column, and a detector configured to detect a component in the sample that has flown through the column, the data-processing device including:

a) an input section configured to allow a user to input information of a schedule table for a plurality of analyses, the schedule table describing a1) an analysis condition including a combination of the values of a plurality of control parameters, a2) the order of execution of the plurality of analyses, and a3) information for identifying a sample to be subjected to each analysis;

b) a control means configured to operate the sample-introducing section according to the schedule table;

c) a chromatogram creating means configured to sequentially receive a series of data collected with the detector during two or more analyses among the plurality of analyses described in the schedule table and to create a joint chromatograms from the series of data if the two or more analyses are scheduled to be continuously performed for the same sample; and d) a display means configured to display the joint chromatogram.

In the data-processing device for a chromatograph according to the present invention, if there is a period of time during which a series of analyses for the same sample are continuously performed, the chromatogram creating means sequentially receives the entire series of data collected with the detector through the series of analyses, and creates a joint chromatogram. The joint chromatogram is displayed on a display screen of the display means. Therefore, for example, if an unnatural discontinuity has been located between a chromatogram obtained by one analysis and a chromatogram obtained by the subsequent analysis, the user can easily detect the discontinuity and suppose that a problem with the device has occurred between one analysis and the subsequent analysis or a falsification of the chromatogram may be made.

In that case, the chromatogram creating means may be configured to progressively create the joint chromatogram with the progress of the plurality of continuously performed analyses. This configuration allows the operator to predict the component contained in the ample or evaluate the appropriateness of the analysis conditions based on the waveform of the joint chromatogram while visually checking the peaks on the joint chromatogram progressively drawn on the display screen of the display, means with the passage of the analyzing time. In other words, the operator can begin to examine the joint chromatogram before the plurality of analyses are entirely completed.

In a preferable mode of the data-processing device for a chromatograph according to the present invention, the chromatograph includes a plurality of columns, a mobile-phase passage into which a sample is to be introduced by the sample-introducing section, and a switching means configured to connect the mobile-phase passage to one of the plurality of columns, and the control means is configured to operate the switching means according to the schedule table.

For example, in the case of analyzing monosaccharides/polyols and sterols contained in the same sample, a certain period of time is required to replace the column between the analysis for the monosaccharides/polyols and the analysis for the sterols. The previously described configuration merely requires the switching of the column connected to the mobile-phase passage to carry out such series of analyses for the same sample. Therefore, the series of analyses can be efficiently and quickly performed to obtain chromatogram data.

In the present invention, when the information concerning the two or more analyses scheduled to be continuously performed for the same sample in the schedule table includes information concerning a standard component contained in the sample, the chromatogram creating means may include:

an individual-chromatogram-data creating means configured to determine, for each analysis in the two or more analyses continuously performed for the same sample, a standard retention time for the analysis from the data collected in the analysis, correct the data based on the standard retention time, and create chromatogram data forming the individual chromatogram corresponding to the analysis; and a joint-chromatogram-data creating means configured to compile the individual chromatogram data into entire chromatogram data forming a joint chromatogram corresponding to the entirety of the two or more analyses continuously performed for the same sample.

If chromatographic analyses are performed under different analysis conditions, even the same component normally shows different retention times depending on the analysis conditions, and therefore, the temporal range of the peak which appears in the chromatogram obtained as the result of each analysis varies depending on the analysis. In the previously described configuration, the retention time of a standard component in each analysis standard retention time) is determined from the data collected in the analysis, and the data forming the chromatogram obtained as the result of the analysis (individual chromatogram data) are corrected with reference to the standard retention time. When there is a variation in the retention time of the same component depending on the analysis, the data obtained by each analysis can be corrected to make the peak corresponding to the same component appear at the corresponding position on each individual chromatogram so that the individual chromatograms can be easily compared with each other. Additionally, the compilation of such individual chromatogram data into a set of chromatogram data covering the entire series of analyses allows for an easy comparison of the peaks of the same component on the joint chromatogram corresponding to a plurality of analyses.

For example, consider the case of analyzing the optical isomers of amino acids using two types of columns, i.e. the CROWNPAK CR-I(+) and CROWNPAK CR-I(—) columns of Daicel Corporation. Using the CROWNPAK CR-I(+) column for the analysis makes the D-forms of amino acids be eluted earlier than their L-forms, thereby enabling the isolation and analysis of a considerable number of constituent amino acids of living organisms. However, D-isoleucine and D-allo-isoleucine cannot be individually detected since they show the same retention behavior in the CROWNPAK CR-I(+) column. On the other hand, using the CROWNPAK CR-I(—) column for the analysis makes the L-forms of amino acids be eluted earlier than their D-forms. This time, the D-isoleucine and D-allo-isoleucine mentioned earlier can be separated, although L-isoleucine and L-allo-isoleucine cannot be individually detected. Accordingly, in the case of the optical isomers of amino acids, all kinds of optical isomers (except for proline) can be individually detected by performing an analysis using the CROWNPAK CR-I(+) column and one using the CROWNPAK CR-I(—) column. In that case, the chromatogram data obtained by the analyses using the two types of columns can be compiled into a single data file by using the data-processing device according to the present invention.

Advantageous Effects of Invention

According to the present invention, in a chromatographic analysis in which fractions of the same sample are sequentially introduced into a column to perform a series of analyses of various components contained in the sample, two or more individual chromatograms which respectively correspond to two or more analyses can be compiled into a single set of chromatogram data and saved. Therefore, analytical processing of the data can be performed on a single set of data. The temporal continuity of the chromatograms obtained by the individual analyses as well as the sameness of the sample can also be guaranteed, so that an abnormality in or falsification of a chromatogram can be easily detected. The task of verifying the validity, authenticity or other aspects of an analysis result can also be more smoothly performed.

BRIEF DESCRIPTION OF DRAWINGS

FIGS. 4A-4C are model diagrams for explaining the operation of correcting a chromatogram based on a standard retention time, where FIGS. 4A and 4B are chromatograms showing results of different analyses performed for the same sample.

FIG. 5A shows chromatograms obtained in the case where the results of analyses using two types of columns (CROWNPAK CR-I(+) and CROWNPAK CR-I(−) columns) were compiled into separate chromatogram data files, while

FIG. 7A is a partially enlarged view of the chromatogram shown in FIG. 5A obtained by using the CROWNPAK CR-I(+) column, while

DESCRIPTION OF EMBODIMENTS

One mode for carrying out the present invention is hereinafter described by means of a concrete embodiment.

Figure 1:
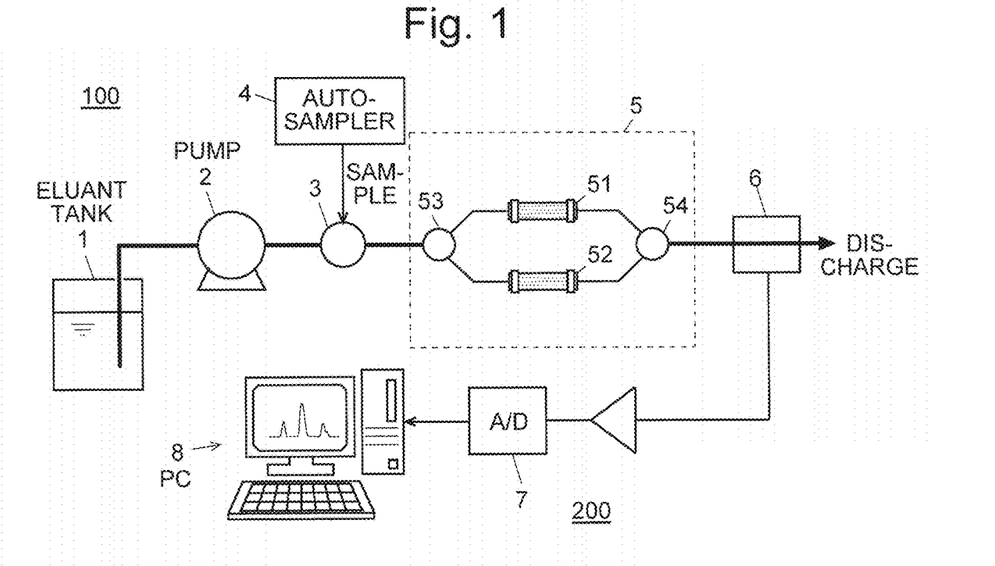
FIG. 1 is an overall configuration diagram of an LC analyzer as one embodiment of a chromatograph equipped with a data-processing device according to the present invention.

FIG. 1 is an overall configuration diagram of an LC analyzer according to the present embodiment. The structure of the present LC analyzer is roughly divided into an LC analysis section 100 for performing an actual analysis for a liquid sample to collect data necessary for analytical data processing, and a data-processing section 200 for performing predetermined waveform processing and computational processing on the collected data to derive a qualitative or quantitative analysis result.

In the LC analysis section 100, an eluant (mobile phase) is drawn from an eluant tank 1 by the operation of a liquid-supply pump 2 and supplied through an auto-injector 3 into a column oven 5 at a fixed flow velocity. A plurality of columns 51 and 52 are provided inside the column oven 5. Passage-switching units 53 and 54 allow for the switching of those columns 51 and 52. An auto-sampler 4 holds a number of samples and selects each of those samples in a predetermined order. The auto-injector 3 injects the selected sample into the eluant at a predetermined timing. This sample is carried by the eluant and introduced into one of the columns 51 and 52. While the sample is passing through the column, the components in the sample are temporally separated.

A detector 6 sequentially detects the sample components eluted from the column 51 or 52 with the passage of time and produces detection signals, which are converted into digital signals by an analogue-to-digital (A/D) converter 7 and sent to a personal computer (which is hereinafter abbreviated as the "PC") 8 serving as the data-processing section. The detector 6 in the present embodiment is a mass spectrometer, although various devices can be used according to the purpose of the analysis. Other examples of the detector 6 include spectrophotometric detectors, spectrofluorometric detectors and conductometric detectors.

Figure 2:
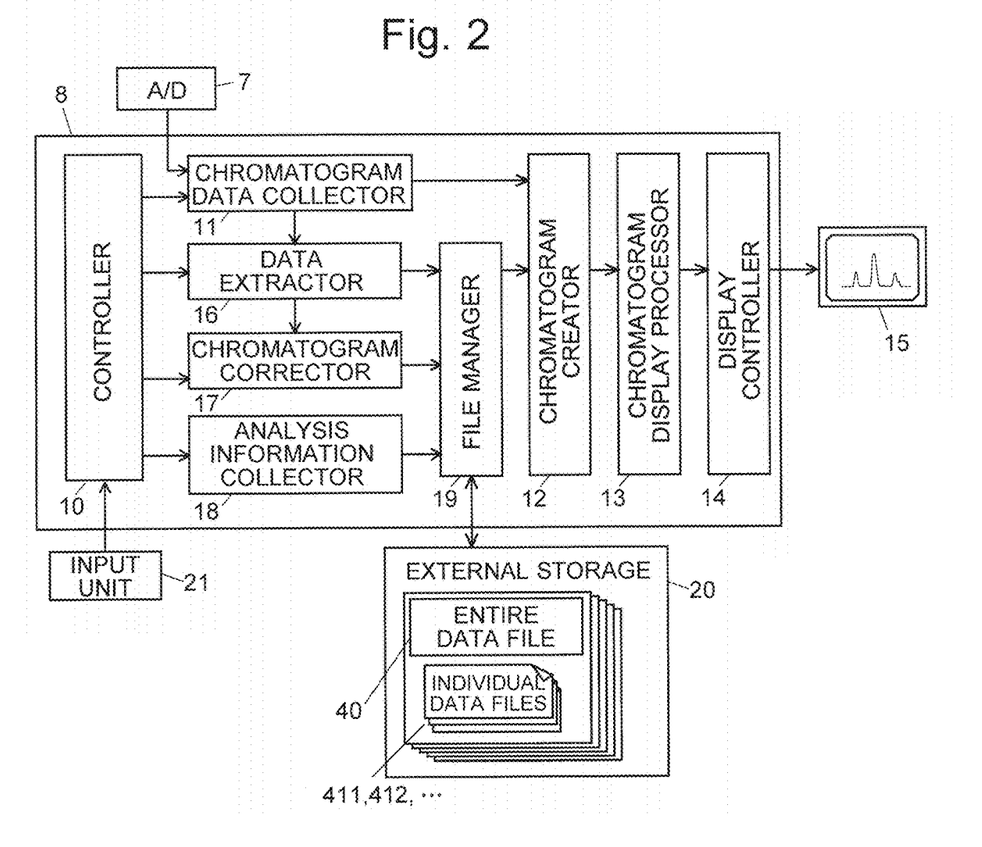
FIG. 2 is a block diagram showing the functional components of the data-processing device according to the present embodiment.

FIG. 2 is a block diagram showing the functional components necessary for achieving the characteristic operation of the data-processing device according to the present embodiment in the PC 8. The detection signals converted into digital signals through the A/D converter 7 are sent to a chromatogram data collector 11. A chromatogram creator 12 performs the predetermined data-processing operation on the signals sequentially fed to the chromatogram data collector 11, to create a series of data forming a chromatogram. The chromatogram is displayed via, a chromatogram display processor 13 and a display controller 14 on the screen of a display unit 15.

Among the data collected in the chromatogram data collector 11, a portion of the data corresponding to a series of continuously performed analyses specified by a controller 10 as will be described later is extracted by a data extractor 16. A chromatogram corrector 17 creates a chromatogram (individual chromatogram) from the data corresponding to each analysis among the data extracted by the data extractor 16, and locates the peak of a standard sample as well as determines the standard retention time from that peak. Based on this standard retention time, the chromatogram corrector 17 recalculates the retention time of each component in the sample and corrects the individual chromatogram. The data forming the corrected individual chromatogram are collected as a set of individual chromatogram data.

An analysis information collector 18 collects various kinds of supplementary information other than the data obtained as analysis results, such as the analysis conditions (the pressure of the liquid-supply pump 2, types of columns 51 and 52, temperature of the column oven 5, etc.), parameters for the data-analyzing process, operation logs showing the operational history, such as a change of the analysis conditions in the middle of the analysis (those kinds of data are hereinafter collectively called the "supplementary analysis information"). The data extractor 16, chromatogram corrector 17 and analysis information collector 18 each transfer the data they have collected under the control of the controller 10 to a file manager 19. The file manager 19 organizes those data into an individual chromatogram data file (which is hereinafter called the "individual data file") and saves the file on an external storage device 20, such as a hard disk drive. The controller 10 compiles the individual data files into a set of data forming a chromatogram corresponding to the entirety of a plurality of analyses continuously performed for the same sample, and saves the data as an entire chromatogram data file (which is hereinafter called the "entire data file") on the external storage device 20. Details of the contents of the entire data file and the individual data file will be described later. The operations of the aforementioned components are controlled by the controller 10. An input unit 21, such as a keyboard and a pointing device (e.g. mouse), is connected to the controller 10.

Figure 3A:
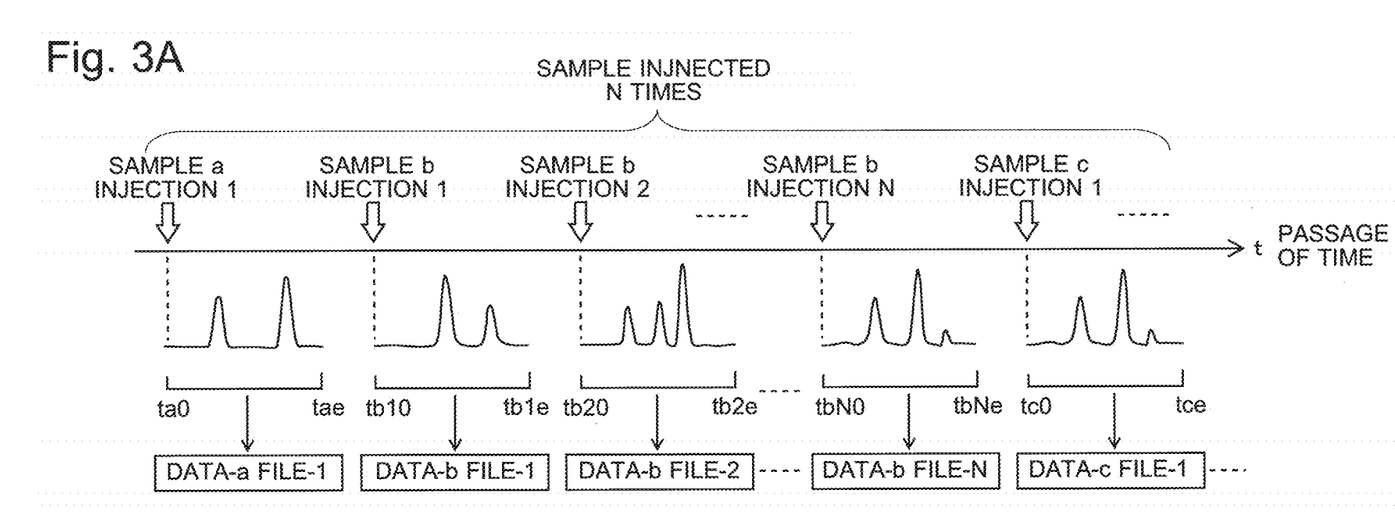
FIG. 3A is a model diagram showing the operation of creating N data files in the case where N analyses have been performed.
Figure 3B:
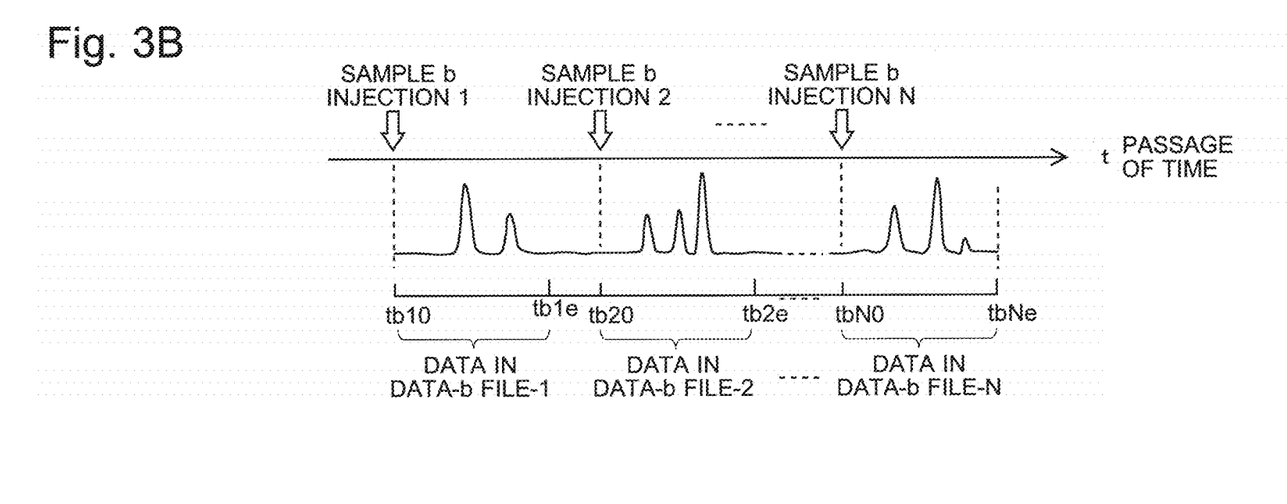
FIG. 3B is a model diagram showing the operation of extracting chromatogram data of a specific sample.
Figure 4A:
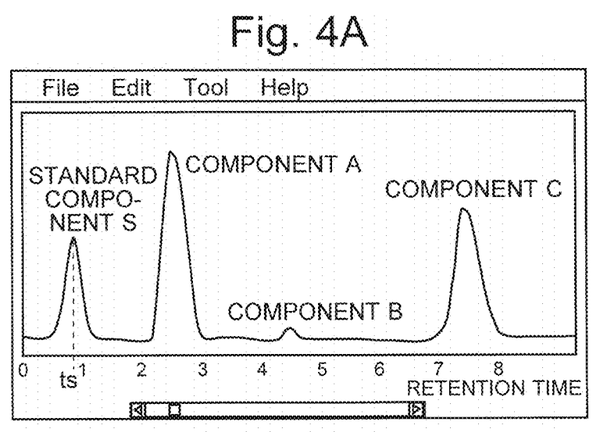
Figure 4B:
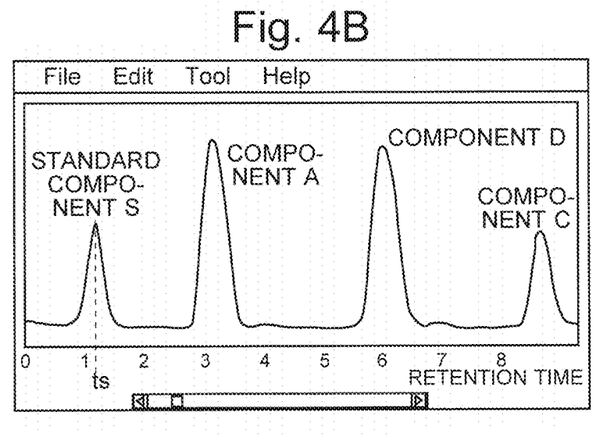
Figure 4C:
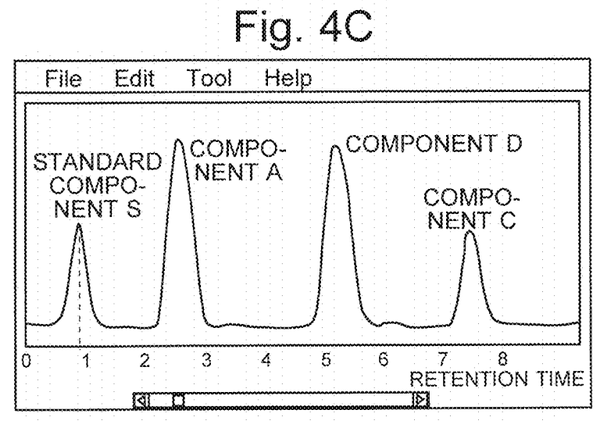
FIG. 4C is a chromatogram obtained by correcting the chromatogram in FIG. 4B based on the standard retention time.

One example of the operation of creating a data file during a series of continuously performed analyses in the LC analyzer having the previously described configuration is hereinafter described with reference to FIGS. 3A, 3B and 4A-4C. FIGS. 3A and 3B are diagrams illustrating the present data-file creating operation. FIGS. 4A-4C are diagrams showing one example of the display screen of the display unit.

In advance of an analysis, an analysis operator using the input unit 21 enters and sets necessary information in the schedule table showing the procedure of the series of analyses. For example, the schedule table includes the sample number, name of the sample, name of the standard component to be added to the sample, amount of sample to be injected, name of the analysis condition file, and other items of information. Those pieces of information determine the sample to be used in each analysis and the analysis conditions for each analysis. The analysis condition file contains information concerning the analysis method (such as the flow velocity of the mobile phase, kind of the mobile phase, and temperature of the column oven) and the analyzing system (such as the type of column). The analysis operator also sets the period of time during which the chromatogram data should be collected, and the period of time during which a series of data for creating a continuous chromatogram should be collected. It should be noted that the period of time for collecting the chromatogram data does not always need to be determined by the analysis operator, but may be determined in any appropriate manner; for example, it may be the period from the beginning of a calibration analysis to the end of the series of analyses, or the period from the beginning point of the first analysis programmed in the schedule table to the ending point of the last analysis, or the period from the log-in to the PC 8 or data-processing software to the log-out of the PC 8 or data-processing software. The period of time for collecting the data for creating the continuous chromatogram may be defined as the period from the beginning to the end of the series of analyses to be continuously performed for a sample when the sample name or sample number has been specified by the analysis operator. The operation for collecting the data for creating the continuous chromatogram may be automatically performed from the beginning to the end of two or more analyses programmed in the schedule table if those analyses are scheduled to be continuously performed for the same sample.

As one example, it is hereinafter assumed that a series of M analyses to be continuously performed with a plurality of samples (samples "a", "b" and "c") sequentially injected are programmed in the schedule table, in which a series of N analyses (M>N) with the analyzing conditions successively changed are scheduled for one of those samples (sample "b"). In this case, a continuous chromatogram should be created from the data obtained from the beginning point of the first analysis to the ending point of the last (Nth) analysis.

When a command for initiating the analysis is issued by the analysis operator, the series of continuously performed analyses are actually initiated. For each of those analyses, the chromatogram data collector 11 collects chromatogram data during the period from the sample injection time t0 to the point in time t1 where a predetermined data-collection period comes to an end (t1-t0), as a series of data to be compiled into a single file. Accordingly, in the case where M analyses are continuously performed, M data files which respectively form M individual chromatograms are created, as shower in 3A, regardless of whether those M analyses are performed for the same sample or different samples. The M data files are sequentially sent to the chromatogram creator 12 at the completion of each analysis, and a chromatogram as the result of each analysis is displayed on the screen of the display unit 15.

Meanwhile, the data extractor 16 receives a command from the controller 10 and extracts a series of data which belong to the period from the beginning time to the ending time of the analyses performed within a period of time specified by the analysis operator among the data collected by the chromatogram data collector 11. For example, in the case where a period of time during which a plurality of analyses for sample "b" should be continuously performed is specified, the chromatogram data collected during the period from the beginning time tb10 of the first analysis for sample "b" to the ending time tbNe of the Nth analysis will be extracted. In that case, the data are extracted as N individual data files in which the data forming the N individual chromatograms are respectively compiled. Consequently, as shown in FIG. 3B, a data file (entire data file) forming a single long-time chromatogram (joint chromatogram) is created in which all chromatograms that show the peaks of various components detected in the N analyses performed for sample "b" are connected in series.

The chromatogram data extracted by the data extractor 16 are sent through the file manager 19 to the chromatogram creator 12, which displays, on the screen of the display unit 15, a chromatogram that is continuously updated with the passage of time.

After the series of analyses for sample "b" have been completed, the chromatogram corrector 17 receives the N individual data files of sample "b" from the data extractor 16 and determines the retention time of the standard component (i.e. the standard retention time) in each analysis from the data forming each individual data file. For example, a plurality of normal alkanes (n-alkanes) having different carbon numbers can be used as the standard components. After the standard retention time in each analysis has been determined, the retention times of the peaks of various components appearing in the chromatograms created from the chromatogram data forming the N individual data files are corrected based on the standard retention time. Additionally, the individual data files in which the retention times of the various peaks have been corrected are compiled into the entire data file forming a chromatogram corresponding to the series of continuously performed analyses.

For example, FIG. 4A is a chromatogram showing the result of one analysis, while FIG. 4B is a chromatogram showing the result of another analysis. The chromatograms in FIGS. 4A and 4B show the results of analyses performed on the same sample. However, due to the difference in analysis conditions, the peaks corresponding to the same component (e.g. the peaks of components "A" and "C") appear within different time ranges. This also applies to the peak of the standard component "S". On the other hand, FIG. 4C shows a chromatogram obtained by correcting the chromatogram in FIG. 4B based on the standard retention time determined from the peak of the standard component "S". A comparison of FIGS. 4A, 4B and 4C demonstrates that the peaks of components "A" and "C" located within different time ranges in the chromatograms before the correction are located at mutually corresponding positions in the chromatograms after the correction. Therefore, the measured results obtained for the same component can be easily compared on the chromatograms although those chromatograms have been obtained by the analyses performed under different analysis conditions.

The analysis information collector 18 collects various kinds of supplementary information related to the analysis, such as the data of the analysis condition file of each analysis specified in the schedule table (or other forms) by the controller 10, an operation log showing the history of the operations performed by the analysis operator through the input unit 21 for changing the analysis conditions (or for other purposes) during the execution of the analysis, or a status log used for monitoring the state of the device during the analysis.

The file manager 19 receives, from the chromatogram corrector 17, the individual data files in which the retention times of the various peaks have been corrected, and compiles those individual data files into a chromatogram data file of the series of continuously performed analyses. Concurrently, the file manager 19 receives the aforementioned pieces of supplementary analysis information from the analysis information collector 18, and prepares an entire data file 40 by including those pieces of information into the same file in a predetermined form. This file is saved on the external storage device 20. The supplement analysis information contained in the entire data file 40 corresponds to all analyses continuously performed for the same sample.

Additionally, the file manager 19 creates individual data files 411, 412, . . . each of which is a single file containing the supplementary analysis information related to each individual analysis in a predetermined form. Those files are related to the entire data file 40 and saved, for example, in the same folder on the external storage device 20.

Thus, the entire data file 40 contains all chromatogram data collected during the execution of a series of analyses continuously performed on the same sample, whereas each individual data file 411, 412, . . . contains chromatogram data which forms a chromatogram obtained by one of the analyses and corresponds to a portion of the data contained in the entire data file 40. The entire data file 40 contains chromatogram data obtained within each period of time interposed between the individual analyses which is not included in any of the individual data files 411, 412, . . . . Therefore, the entire data file 40 can be used for the checking of the continuity of the analyses or preparation of a summary report on the entire series of the analyses.

On the other hand, each individual data file 411, 412, . . . contains supplementary analysis information, such as the parameters required for analytically processing the chromatogram data. With such a file, the waveform processing of the chromatogram and the quantitative calculation can be performed.

Figure 5A:
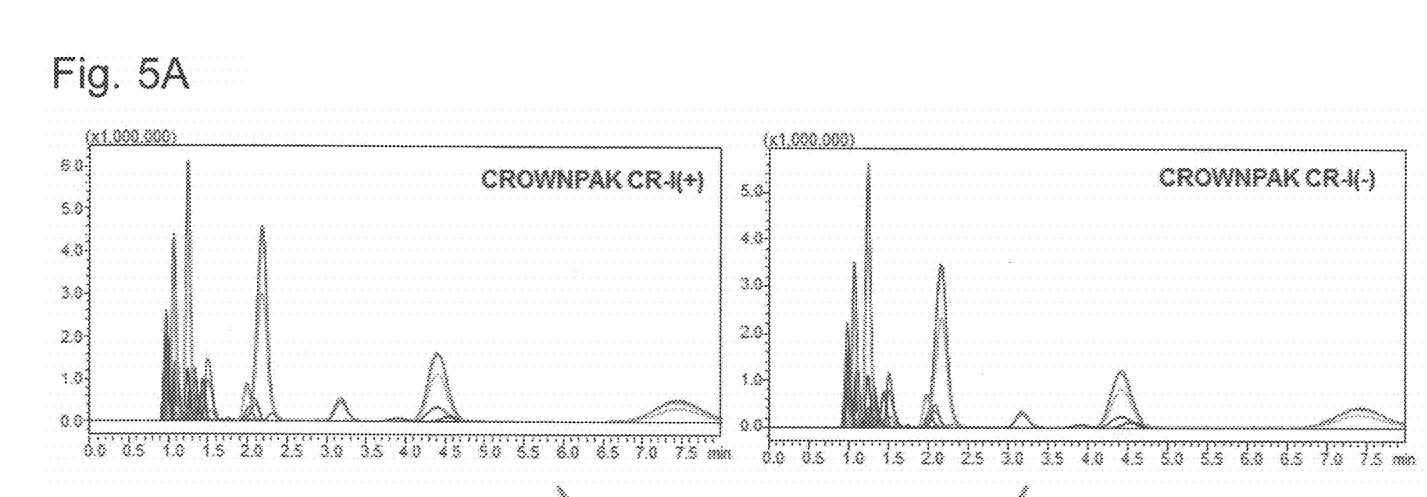
Figure 5B:
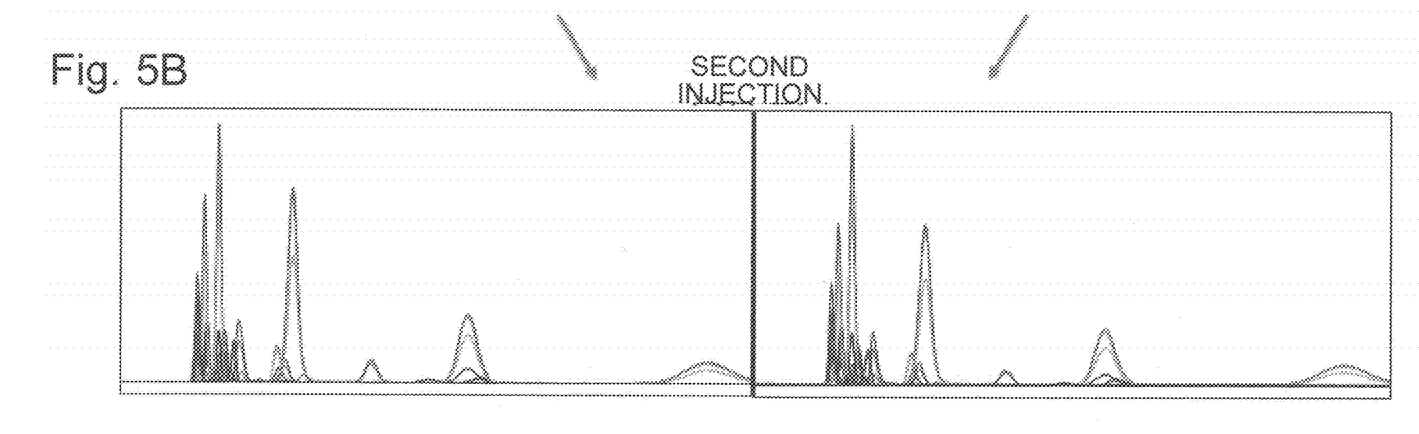
FIG. 5B shows a chromatogram obtained in the case where the same analysis results were compiled into a single chromatogram data file.
Figure 6A:
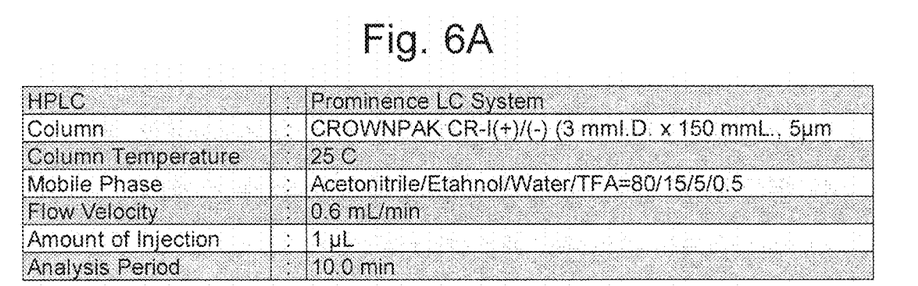
FIG. 6A is a table showing analysis conditions of an LC analysis section.
Figure 6B:
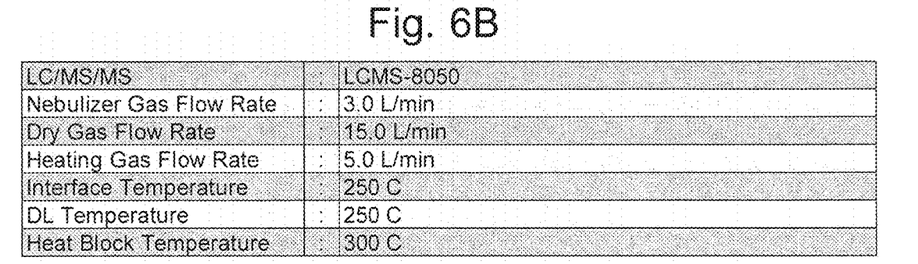
FIG. 6B is a table showing analysis conditions of a mass spectrometer.
Figure 7A:
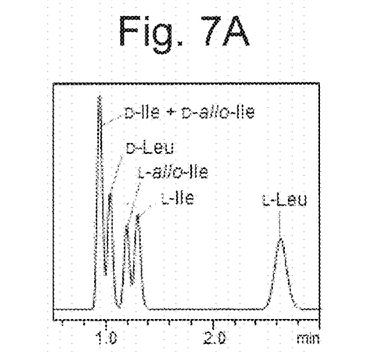
Figure 7B:
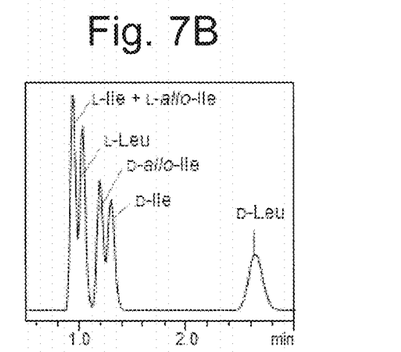
FIG. 7B is a partially enlarged view of the chromatogram shown in FIG. 5A obtained by using the CROWNPAK CR-I(-) column.

FIGS. 5A and 5B show the results of analyses (LC-MS/MS analyses) performed on the amino acids contained in a fermented food product using two types of columns (CROWNPAK CR-I(+) and CROWNPAK CR-I(—) columns). FIGS. 6A and 6B show the analysis conditions and other pieces information used in the LC analysis section 100 and the detector 6 (mass spectrometer). Specifically, FIG. 5A shows chromatograms obtained from two chromatogram data files individually created from the results of the analyses using the two types of columns. Regardless of whether the CROWNPAK CR-I(+) or CROWNPAK CR-I(—) column is used, the 22 kinds of amino acids can be detected with sufficient levels of sensitivity. However, not all amino acids are successfully separated into the D-form and L-form for the detection. For example, FIG. 7A is a partially enlarged view of the chromatogram shown in FIG. 5A obtained by using the CROWNPAK CR-I(+) column, and FIG. 7B is a partially enlarged view of the chromatogram shown in FIG. 5A obtained by using the CROWNPAK CR-I(-) column. As is evident from FIGS. 7A and 7B, D-Ile and D-allo-Ile appear to be a single peak when the CROWNPAK CR-I(+) column is used, while L-Ile and L-allo-Ile appear to be a single peak when the CROWNPAK CR-I(-) column is used. In such a case, those chromatograms must be individually analyzed using different data-analysis methods, with one method prepared for analyzing D/L-Ile and the other for D/L-allo-Ile.

By comparison, FIG. 5B shows a chromatogram obtained from a single chromatogram data file into which the results of the analyses using the two types of columns were compiled in the case of FIG. 5B, since the two chromatograms are combined into a single chromatogram, the entire data can be analyzed with a single data-analysis method. In this case, some amino acids will have two peaks appearing on the single chromatogram, of which the user may designate one peak as the target for the analysis, or a peak having a higher level of reproducibility may be previously set as the target. It is also possible to subject each of the two peaks to the data analysis and calculate an average of the obtained results.

It should be noted that the previously described embodiment is a mere example of the present invention, and any change, addition or the like appropriately made within the spirit of the present invention will evidently fall within the scope of the present invention.

For example, after the completion of a series of analyses for the same sample, the file manager 19 may receive the individual data files from the chromatogram data collector 11, compile those files into an entire data file, as well as save the individual data files and the entire data file on the external storage device 20 after adding the supplementary analysis information to each of those files.

As another example, the single chromatogram may be created from the data collected in a portion of the series of analyses performed on the same sample.

REFERENCE SIGNS LIST

6 . . . Detector
11 . . . Chromatogram Data Collector
12 . . . Chromatogram Creator
13 . . . Chromatogram Display Processor
14 . . . Display Controller
15 . . . Display Unit
16 . . . Data Extractor
17 . . . Chromatogram Corrector
18 . . . Analysis Information Collector
19 . . . File Manager
20 . . . External Storage Device
21 . . . Input Unit
40 . . . Entire Data File
411 . . . Individual Data File
51 . . . Column
52 . . . Column
53 . . . Passage-Switching Unit
100 . . . LC Analysis Section
200 . . . Data-Processing Section

The invention claimed is:

1. A data-processing device to be used for a chromatograph including a column, a sample-introducing section configured to introduce a sample into the column, and a detector configured to detect a component in the sample that has flown through the column, the data-processing device comprising:
 a) an input section configured to allow a user to input information of a schedule table for a plurality of analyses to be performed under different conditions, the schedule table describing a1) an analysis condition of each analysis including a combination of values of a plurality of control parameters, a2) an order of execution of the plurality of analyses, and a3) information for identifying a sample to be subjected to each analysis, wherein the plurality of analyses includes analyses which are continuously performed on a single sample, wherein each of the plurality of analyses are performed under different conditions of separating components contained in the single sample;
 b) controller configured to operate the sample-introducing section according to the schedule table;
 c) a chromatogram creator configured to sequentially receive a series of data collected with the detector during two or more analyses among the plurality of analyses described in the schedule table and to create a joint chromatogram from the series of data when the two or more analyses are scheduled to be continuously performed for the single sample; and
 d) a display configured to display the joint chromatogram.

2. The data-processing device for a chromatograph according to claim 1, wherein:
 the chromatogram creator is configured to create the joint chromatogram which changes with a progress of a plurality of continuously performed analyses.

3. The data-processing device for a chromatograph according to claim 1, wherein:
 the chromatograph includes a plurality of columns, a mobile-phase passage into which a sample is to be introduced by the sample-introducing section, and a switcher configured to connect the mobile-phase passage to one of the plurality of columns,
 the controller is configured to operate the switcher according to the schedule table, and
 the two or more analyses are to be performed under different analyzing systems corresponding to the plurality of columns.

4. The data-processing device for a chromatograph according to claim 1, wherein:
 when information concerning the two or more analyses scheduled to be continuously performed for the single sample in the schedule table includes information concerning a standard component contained in the sample, the chromatogram creator comprises:
 an individual-chromatogram-data creator configured to determine, for each analysis in the two or more analyses continuously performed for the single sample, a standard retention time for the analysis from the series of data collected in the analysis, correct the series of data based on the standard retention time, and create chromatogram data forming the individual chromatogram corresponding to the analysis; and
 a joint-chromatogram-data creator configured to compile the individual chromatogram data into entire chromatogram data forming a joint chromatogram corresponding to an entirety of the two or more analyses continuously performed for the single sample.

5. The data-processing device for a chromatograph according to claim 3, wherein:
 the plurality of columns include a plurality of kinds of columns which differ from each other in separation characteristics, the plurality of kinds of columns being capable of separating a plurality of kinds of amino acids contained in a sample as well as separating a D-form and an L-form of at least one amino acid in the plurality of kinds of amino acids.

6. The data-processing device for a chromatograph according to claim 3, wherein:
 the chromatogram creator being configured to sequentially receive the series of data collected with the detector during the two or more analyses among the plurality of analyses described in the schedule table includes being configured to receive all data collected with the detector during a time period in which the two or more analyses among the plurality of analyses described in the schedule table are continuously performed; and the chromatogram creator being configured to create a joint chromatogram from the series of data if the two or more analyses are scheduled to be continuously performed for the single sample includes being configured to create a joint chromatogram from the all data if the two or more analyses using different columns among the plurality of columns are scheduled to be continuously performed for the single sample.

* * * * *